United States Patent [19]

Schneider

[11] 4,025,515
[45] May 24, 1977

[54] 6-CHLORO-2,4-DIAMINOPYRIMIDINES

[75] Inventor: Rupert Schneider, Riehen, Switzerland

[73] Assignee: Sandoz Ltd., Basel, Switzerland

[22] Filed: Mar. 7, 1975

[21] Appl. No.: 556,304

Related U.S. Application Data

[63] Continuation of Ser. No. 435,222, Jan. 21, 1974, abandoned, which is a continuation-in-part of Ser. No. 174,568, Aug. 24, 1971, Pat. No. 3,892,554, which is a continuation-in-part of Ser. No. 10,056, Feb. 9, 1970, abandoned.

[30] Foreign Application Priority Data

Feb. 14, 1969  Switzerland ............... 2234/69

[52] U.S. Cl. .................................. 260/256.4 N
[51] Int. Cl.² .................................. C07D 239/30
[58] Field of Search ................... 260/256.4 N

[56] References Cited

UNITED STATES PATENTS

| 3,118,754 | 1/1964 | Nickell .................................. 71/92 |
| 3,284,188 | 11/1966 | Amagasa et al. ...................... 71/92 |

FOREIGN PATENTS OR APPLICATIONS

| 745,903 | 8/1970 | Belgium ................................. 71/92 |
| 1,170,743 | 9/1958 | France .................................. 71/92 |
| 662,501 | 4/1964 | Italy ..................................... 71/92 |
| 347,672 | 8/1960 | Switzerland .......................... 71/92 |

OTHER PUBLICATIONS

Forrest et al., J. Chem. Soc., pp. 3–7 (1951).
Noell et al., J. Med. Pharm., 5, pp. 559–588 (1962).

*Primary Examiner*—Paul M. Coughlan, Jr.
*Attorney, Agent, or Firm*—Gerald D. Sharkin; Richard E. Vila

[57] ABSTRACT

The invention concerns pyrimidine derivatives of the formula:

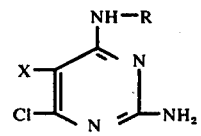

in which X is hydrogen or chlorine and R is alkyl or cycloalkyl, in free base or agriculturally acceptable acid addition salt form.

The compounds possess herbicidal activity.

10 Claims, No Drawings

6-CHLORO-2,4-DIAMINOPYRIMIDINES

This is a continuation of abandoned application Ser. No. 435,222, filed Jan. 21, 1974, which is a continuation-in-part of application Ser. No. 174,568, filed Aug. 24, 1971, now U.S. Pat. No. 3,892,554, which is itself a continuation-in-part of abandoned application Ser. No. 10,056, filed Feb. 9, 1970.

The present invention relates to pyrimidine derivatives.

This invention provides herbicidally active compounds of formula I,

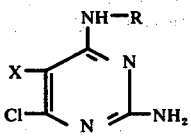    I wherein
X is hydrogen or halogen, preferably chlorine, and
R is alkyl of 2 to 6 carbon atoms, alkenyl of 3 to 6 carbon atoms or cycloalkyl of 5 or 6 ring carbon atoms, especially the compounds of formula I, wherein X is hydrogen or chlorine and R is branched chain alkyl of 3 or 4 carbon atoms, straight or branched chain alkyl of 5 or 6 carbon atoms or cycloalkyl of 5 or 6 carbon atoms, or when X is chlorine, then R may also be straight chain alkyl of 3 or 4 carbon atoms.

The compounds may be produced as follows, viz:
a. reacting a compound of formula II,

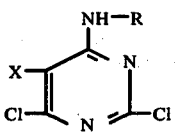    II wherein R and X are as defined above, with ammonia, or
b. producing a compound of formula Ia,

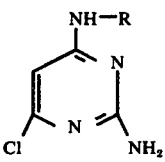    Ia wherein R is as defined above, by reacting a compound of formula III,

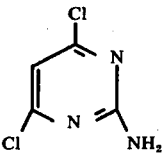    III with an amine of formula IV,

    IV wherein R is as defined above, or
c. producing a compound of formula Ib,

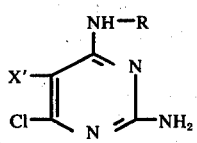    Ib wherein X' is chlorine, and R is as defined above, by chlorinating a compound of formula Ia defined above, Process a) may, for example, be effected with a concentrated aqueous ammonia solution, and suitably in a water-miscible organic solvent which is inert under the reaction conditions, e.g. an alcohol. The process is suitably effected at a temperature of from 100° to to 180° C, preferably 120° to 160° C. The process may desirably be carried out in a pressure vessel.

Process b) may be effected in conventional manner for example in an organic solvent which is inert under the reaction conditions, e.g. an alcohol, and at the reflux temperature of the reaction mixture. Suitably, the compounds of formula III and IV may be employed in a molar ratio of 1:2.

Process c) may be effected in conventional manner.

The resulting compounds of formula I may be isolated and purified in conventional manner. Where required, free base forms of the compounds of formula I may be converted to acid addition salt forms in conventional manner, and, likewise, vice versa.

Examples of agriculturally acceptable acid addition salt forms of the compounds of formula I are the methane sulphonates, hydrogen sulphates, hydrochlorides, hydrobromides, phosphates and trichloroacetates.

The compounds of formula II employed as starting materials in process c) may be produced by reacting a compound of formula V,

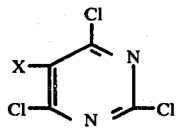    V wherein X is as defined above, with a compound of formula IV stated above.

The process may be effected in conventional manner, for example in an organic solvent which is inert under the reaction conditions. It is suitably effected at room temperature or slightly elevated temperature and the reaction time may typically vary from ½ to 2 hours. This process may lead to a mixture of the desired compounds of formula II and other aminated pyrimidines. The compounds of formula II may then be isolated, for example, by steam distillation.

The compounds of formulae III, IV and V are either known or may be produced in manner known per se.

The compounds of formula I in free base or agriculturally acceptable acid addition salt form are useful because they possess herbicidal activity against the growth of weeds, in particular against dicotyledonous weeds, e.g. *Plantago lanceolata*, *Amaranthus retroflexus*, *Capsella bursa-pastoris*, *Chenopodium album*, *Galium aparine*, *Stellaria media* and *Senecio vulgaris*, as well as against undesired grasses, for example *Echinochloa crus-galli*, *Alopecurus pratensis* and *Setaria sp*.

The compounds are furthermore useful because they exhibit selectivity against weeds amidst cultivated plants. Thus, for example, maize, wheat, potatoes, onions and leeks are not significantly damaged by the use of the herbicides of the invention, either before or after, and particularly after, emergence of the cultured plants and the weeds.

For the abovementioned use, in general, the compounds of the invention may be applied to a cultivated plant locus in an amount of from 1 to 12 kg, preferably 2 to 6 kg, per hectare.

For use as herbicides, the compounds of formula I in free base or agriculturally acceptable acid addition salt form may be formulated into suitable compositions, e.g. suspensions, emulsions, pastes and granules. The herbicidal compositions may be produced, for example, by intimately mixing or grinding the compounds of formula I with a suitable carrier, optionally with the addition of dispersing agents or a solvent which is inert to the active agent.

In order to produce compositions which can be applied in solid form, e.g. dusting and strewing powders and granulates, the compounds of the invention may be mixed with solid carriers, e.g. kaolin, talc, chalk and limestone.

Substances improving adhesiveness, wettability and dispersibility may also be incorporated into the compositions.

Spraying powders may be obtained by mixing and grinding the compounds with a powdery carrier material until the mixture is homogeneous. The powdery carrier may for example be kaolin, talc, chalk, limestone and cellulose powder.

In order to produce liquid forms of the composition, one or more compounds of the invention are dissolved in an organic solvent or solvent mixture or water. Examples of suitable organic solvents are ketones such as acetone, alcohols, hydrocarbons, chlorinated hydrocarbons and alkyl naphthalenes, alone or in admixture.

For special purposes, the compounds of the invention may be combined with other herbicides, e.g. of the urea class, saturated or unsaturated halogen fatty acids, halogen benzonitriles, halogen benzoic acids, phenoxyalkyl carboxylic acids, carbamates and triazines.

Application forms of compositions containing compounds of formula I or their agriculturally acceptable acid addition salts as active agent generally contain 0.01 to 10 % by weight of active agent. Concentrates generally contain 5 to 50 % by weight of active agent.

The herbicidal compositions can, for example, be applied as a liquid spray or a dust to the plant locus to be protected from the weeds. Such application can be made directly to the locus, pre- or post- emergence of the weeds.

The preferred compound of the invention is 2-amino-4-isopropylamino-6-chloropyrimidine, particularly in free base form. Particularly effective agriculturally acceptable acid addition salt forms thereof are the hydrogen chloride and trichloroacetate forms.

In the following Examples a and b, which illustrate application forms of the herbicides of the invention, parts are by weight.

EXAMPLE a 10 parts of 2-amino-4-isopropylamino-6-chloropyrimidine are mixed with 25 parts of isoctylphenyl decaglycol ether and 65 parts of acetone. The resulting emulsion is diluted with water to the desired concentration before use.

EXAMPLE b 25 parts of 2-amino-4-(2-n-hexylamino)-6-chloropyrimidine hydrochloride are mixed with 5 parts of a condensation product of formaldehyde and naphthalene sulphonate, 2 parts of alkylbenzene sulphonate, 5 parts of dextrin, 1 part of ammonium caseinate and 62 parts of diatomaceous earth until a homogeneous mixture results and this is subsequently ground until the particles are considerably smaller than 45 microns. This formulation is diluted with water to the desired concentration before use.

The herbicidal effect of the compounds of formula I, in free base and agriculturally acceptable acid addition salt form, is indicated in the following Table. The scale 1 to 9 employed in the Table signifies: 1 = no destruction, 9 = total destruction. The following Table shows the effect of post-emergence treatment with 3 kg of active agent per hectare.

The Table shows the herbicidal effect of the agents of the invention and also their selectivity in culturing plants, e.g. maize.

| Active ingredient of the herbicide | Amaranthus retroflexus | Capsella bursa-pastoris | Chenopodium album | Calium aparine | Stellaria media | Senecio vulgaris | Echinochloa crusgalli | Maize |
|---|---|---|---|---|---|---|---|---|
| 2-amino-4-isopropylamino-6-chloro-pyrimidine | 9 | 9 | 9 | 7 | 9 | 9 | 9 | 1 |
| 2-amino-4-isopropylamino-6-chloro-pyrimidine hydrochloride | 9 | 9 | 9 | 9 | 9 | 9 | 9 | 1 |
| 2-amino-4-isopropylamino-6-chloro-pyrimidine trichloroacetate | 9 | 9 | 9 | 7 | 9 | 9 | 9 | 1 |
| 2-amino-4-isobutylamino-6-chloro-pyrimidine | 9 | 9 | 9 | 6 | 9 | 9 | 7 | 1 |
| 2-amino-4-pentylamino-6-chloro-pyrimidine | 9 | 9 | 6 | 9 | 9 | 9 | 9 | 1 |
| 2-amino-4-cyclohexylamino-6-chloro-pyrimidine | 9 | 9 | 6 | 9 | 9 | 9 | 9 | 1 |
| 2-amino-4-n-hexylamino-6-chloro-pyrimidine | 9 | 9 | 9 | 9 | 9 | 9 | 9 | 1 |
| 2-amino-4-sec-butylamino-6-chloro-pyrimidine | 9 | 9 | 9 | 9 | 9 | 9 | 9 | 1 |

The following Examples illustrate the production of the new compounds. The temperatures are indicated in degrees Centigrade.

EXAMPLE 1

2-Amino-4-isopropylamino-6-chloro-pyrimidine 400 (2.18 mols) of 2,4,6-trichloro-pyrimidine are dissolved in 2000 cc of alcohol. 280 g (4.75 mols) of isopropyl amine in 200 cc of alcohol are added to the solution while stirring and cooling, the temperature being maintained below 30°. The mixture is subsequently stirred at room temperature for a further 60 minutes and the alcohol is then removed by evaporation in a water jet vacuum until the mixture hardens to a solid mass. The solid residue is washed with water and subjected to steam distillation. This distillation is continued until only traces of the steam-volatile 2-isopropylamino-4,6-dichloro-pyrimidine are deposited in the receiver. The steam-nonvolatile 4-isopropylamino-2,6-dichloro-pyrimidine is obtained. After distillation in a vacuum (B.P. 124°/0.1 mm of Hg) the pure product, having a M.P. of 69°–70° after recrystallization from water/alcohol, is obtained.

30 g (0.15 mols) of 4-isopropylamino-2,6-di-chloro-pyrimidine in 100 cc of alcohol are mixed with 50 cc of a 23 % aqueous ammonia solution and the mixture is heated to 140° in an autoclave for 4 hours. The reaction mixture is subsequently evaporated to dryness in a vacuum, the solid residue is taken up in 300 cc of chloroform and washed thrice with 200 cc amounts of water. After drying with aluminium oxide and removing the chloroform by evaporation a viscous oil is obtained which solidifies slowly. The resulting 2-amino-4-isopropylamino-6-chloro-pyrimidine has a M.P. of 114°–116° after recrystallization from benzene/petroleum ether.

Analysis: $C_7H_{11}ClN_4$. Molecular weight: 186.7. Calc: C 45.1 H 6.0 N 30.0 Cl 19.0 %. Found: 45.4 6.1 29.8 18.8 %.

In analogous manner to that described in Example 1, 2-amino-4-iso-pentylamino-6-chloro-pyrimidine and 2-amino-4-cyclopentylamino-6-chloro-pyrimidine may be produced. Isolation and purification may be effected in conventional manner.

EXAMPLE 2

2-Amino-4-isopropylamino-6-chloro-pyrimidine 600 g of 2-amino-4,6-dichloro-pyrimidine (3.66 mols) are added to 3000 cc of alcohol, 395 g of isopropylamine (8.05 mols) are added, and the mixture is slowly heated to 80° during the course of 2 hours while stirring. After the material is dissolved, the solution is heated under reflux for 3 hours. The alcohol is then distilled off and the residue dissolved in dilute sulphuric acid. The solution must give a clearly acid reaction. The solution is shaken out several times with chloroform. A layer of 3000 cc of chloroform is subsequently placed under the aqueous solution and the solution is made alkaline with a caustic soda solution (pH 11), whereby the temperature should not exceed 35°. After shaking out the chloroform phase is separated and the aqueous phase is again shaken out with chloroform. The combined chloroform solution is dried with Glauber's salt after washing with water and the chloroform is evaporated. After standing for a short time, the oily residue crystallizes. The product may be recrystallized as described in Example 1 for purposes of purification.

EXAMPLE 3

2-Amino-4-isopropylamino-5,6-dichloro-pyrimidine 20 g (0.1 mol) of 2-amino-4-isopropylamino-6-chloro-pyrimidine in 250 cc of carbon tetrachloride are heated to reflux temperature while stirring. As soon as a clear solution results, chlorine is slowly passed through the solution until the taking up of chlorine stops. After about 90 minutes, the solution is cooled, the precipitated material is filtered with suction and washed with carbon tetrachloride. The product may be recrystallized from dioxane, M.P. 193° (decomp.).

Analysis: $C_7H_{10}Cl_2N_4$. Molecular weight: 221. Calc.: C 38.0 H 4.6 Cl 32.1 N 25.3 %. Found: 38.4 4.8 31.7 25.1 %.

In analogous manner to that described in Example 3, 2-amino-4-n-propylamino-5,6-dichloro-pyrimidine and 2-amino-4-n-butylamino-5,6-dichloro-pyrimidine may be produced. Isolation and purification may be effected in conventional manner.

The following compounds may be obtained in a manner analogous to that described in Examples 1 and 2:

| Ex. No. | | Formula | Molecular weight | Melting point | Analysis % Calculated Found | | | |
|---|---|---|---|---|---|---|---|---|
| | | | | | C | H | Cl | N |
| 4 | 2-amino-4-n-hexylamino-6-chloro-pyrimidine | $C_{10}H_{17}ClN_4$ | 228,7 | 95–96° | 52,5 53,0 | 7,5 7,4 | 15,5 15,1 | 24,5 23,9 |
| 5 | 2-amino-4-cyclohexylamino-6-chloro-pyrimidine | $C_{10}H_{15}ClN_4$ | 225,7 | 138–140° | 53,2 53,5 | 6,3 6,4 | 15,7 15,4 | 24,8 24,6 |
| 6 | 2-amino-4-sec-butylamino-6-chloro-pyrimidine | $C_8H_{13}ClN_4$ | 200,7 | 96–97° | 47,9 48,5 | 6,5 6,4 | 17,7 18,0 | 27,9 27,3 |
| 7 | 2-amino-4-isobutylamino-6-chloro-pyrimidine | $C_8H_{13}ClN_4$ | 200,7 | 108–109° | 47,9 48,1 | 6,5 6,8 | 17,7 17,7 | 27,9 28,1 |
| 8 | 2-amino-4-n-pentylamino-6-chloro-pyrimidine | $C_9H_{15}ClN_4$ | 214,7 | 95–96° | 50,3 49,7 | 7,0 7,3 | 16,5 16,8 | 26,1 26,2 |
| 9 | 2-amino-4-tert-butylamino-6-chloro-pyrimidine | $C_8H_{13}ClN_4$ | 200,7 | 141–142° | 47,9 48,1 | 6,5 6,0 | 17,7 17,2 | 27,9 28,0 |

The agriculturally acceptable acid addition salts of the compounds of formula I, which are also included within the scope of the present invention, may be produced in conventional manner, e.g.: Trichloroacetate of 2-amino-4-isopropylamino-6-chloro-pyrimidine.

18.6 g (0.1 mol) of 2-amino-4-isopropylamino-6-chloro-pyrimidine are dissolved in 100 cc of alcohol and 18 g (0.11 mols) of trichloroacetic acid are added while cooling. The mixture is evaporated to dryness in a vacuum and the resulting solid, colourless residue is recrystallized from alcohol. The trichloroacetate has a melting point of 150°–152°.

Analysis: $C_7H_{11}ClN_4.HO_2CCl_3$ Molecular weight: 350. Calc.: C 30.9 H 3.5 Cl 40.5 N 16.0 %. Found: 31.0 3.5 39.6 16.6 %.

Hydrochloride of 2-amino-4-isopropylamino-6-chloro-pyrimidine.

18.6 g (0.1 mol) of 2-amino-4-isopropylamino-6-chloro-pyrimidine are dissolved in 100 cc of alcohol and 11 g (0.11 mols) of 36 % hydrochloric acid are added while cooling. The mixture is evaporated to dryness in a vacuum and the resulting solid, colourless residue is recrystallized from alcohol. The hydrochloride has a melting point of 235°–236°.

Analysis: $C_7H_{11}ClN_4 \cdot HCl$ Molecular weight: 223. Calc.: C 37.7 H 5.4 Cl 31.7 N 25.0 %. Found: 37.7 5.4 31.8 25.1 %.

Methanesulphonate of 2-amino-4-sec.butylamino-6-chloro-pyrimidine.

20.0 g (0.1 mol) of 2-amino-4-sec.butylamino-6-chloro-pyrimidine are dissolved in 100 cc of alcohol and 10.5 g (0.11 mols) of methanesulphonic acid are added to the solution with cooling. The mixture is evaporated to dryness in a vacuum. The resulting solid, very hygroscopic, colourless residue has a M.P. of 116°–118°.

Analysis: $C_8H_{13}ClN_4 \cdot CH_3SO_3H$ Molecular weight: 296.5. Calc.: C 36.5 H 5.7 Cl 11.9 N 18.9 S 10.8 %. Found: 36.8 5.4 12.0 19.3 10.3 %.

Hydrogen sulphate of 2-amino-4-sec.butylamino-6-chloro-pyrimidine.

20.0 g (0.1 mol) of 2-amino-4-sec.butylamino-6-chloro-pyrimidine are dissolved in 100 cc of alcohol and 10.8 g (0.11 mols) of sulphuric acid are added to the solution with cooling. The mixture is evaporated to dryness in a vacuum. The resulting solid, very hygroscopic, colourless residue has a M.P. of 95°–105°.

Analysis $C_8H_{13}ClN_4 \cdot H_2SO_4$ Molecular weight: 298.5. Calc.: C 32.9 H 5.0 Cl 11.9 N 18.8 S 10.7 %. Found: 32.5 4.8 12.0 19.0 10.7 %.

Phosphate of 2-amino-4-sec.butylamino-6-chloro-pyrimidine.

20.0 g (0.1 mol) of 2-amino-4-sec.butylamino-6-chloro-pyrimidine are dissolved in 100 cc of alcohol and 10.8 g (0.11 mols) of phosphoric acid are added to the solution with cooling. The mixture is evaporated to dryness in a vacuum and the resulting solid, colourless residue is recrystallized from alcohol or acetonitrile. M.P. 176°.

Analysis: $C_8H_{13}ClN_4 \cdot H_2SO_4$ Molecular weight: 198.5. Calc.: C 32.9 H 5.0 Cl 11.9 N 18.8 S 10.7%. Found: 32.5 4.8 12.0 19.0 10.7%.

Hydrochloride of 2-amino-4-isobutylamino-6-chloro-pyrimidine.

20.0 g (0.1 mol) of 2-amino-4-isobutylamino-6-chloro-pyrimidine are dissolved in 100 cc of alcohol and 11 g (0.11 mols) of 36.5 % hydrochloric acid are added to the solution with cooling. The mixture is evaporated to dryness in a vacuum and the resulting solid, colourless residue is recrystallized from alcohol or acetonitrile. M.P. 241°.

Analysis: $C_8H_{13}ClN_4 \cdot HCl$. Molecular weight: 237. Calc.: C 40.5 H 5.9 Cl 30.0 N 23.6 %. Found: 40.7 6.3 29.8 23.0 %.

Trichloroacetate of 2-amino-4-isobutylamino-6-chloro-pyrimidine.

20.0 g (0.1 mol) of 2-amino-4-isobutylamino-6-chloro-pyrimidine are dissolved in 100 cc of alcohol and 18 g (0.11 mols) of trichloroacetic acid are added to the solution with cooling. The mixture is evaporated to dryness in a vacuum and the resulting solid, colourless residue is recrystallized from alcohol or acetonnitrile. M.P. 149°.

Analysis: $C_8H_{13}ClN_4 \cdot CCl_3COOH$. Molecular weight: 364. Calc.: C 33.0 H 3.8 Cl 39.0 N 15.4 %. Found: 33.1 4.1 39.0 15.1 %.

What is claimed is:

1. A compound of the formula:

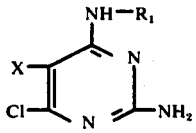

wherein
X is hydrogen or chloro, and
$R_1$ is isopropyl, isobutyl, sec. - butyl, tert. - butyl, n-pentyl, n-hexyl or cyclohexyl, with the proviso that $R_1$ is isopropyl when X is chloro,
or an agriculturally acceptable acid addition salt thereof.

2. A compound of claim 1, wherein X is hydrogen.

3. The compound of claim 1, which is 2-amino-4-isopropylamino-6-chloro-pyrimidine.

4. The compound of claim 1, which is 2-amino-4-n-hexylamino-6-chloro-pyrimidine.

5. The compound of claim 1, which is 2-amino-4-sec.butylamino-6-chloro-pyrimidine.

6. The compound of claim 1, which is 2-amino-4-isobutylamino-6-chloro-pyrimidine.

7. The compound of claim 1, which is 2-amino-4-n-pentylamino-6-chloro-pyrimidine.

8. The compound of claim 1, which is 2-amino-4-tert-.butylamino-6-chloro-pyrimidine.

9. The compound of claim 1, which is 2-amino-4-cyclohexylamino-6-chloro-pyrimidine.

10. The compound of claim 1, which is 2-amino-4-isopropylamino-5,6-dichloro-pyrimidine.

* * * * *